US 8,227,244 B2

United States Patent
Fuchs et al.

(10) Patent No.: US 8,227,244 B2
(45) Date of Patent: Jul. 24, 2012

(54) METHOD FOR ISOLATING DERMAL PAPILLA CELLS AND USES THEREOF

(75) Inventors: Elaine Fuchs, New York, NY (US); Michael Rendi, New York, NY (US)

(73) Assignee: The Rockefeller University, New York, NY (US)

( * ) Notice: Subject to any disclaimer, the term of this patent is extended or adjusted under 35 U.S.C. 154(b) by 864 days.

(21) Appl. No.: 11/914,402

(22) PCT Filed: May 8, 2006

(86) PCT No.: PCT/US2006/017658
§ 371 (c)(1),
(2), (4) Date: Feb. 20, 2008

(87) PCT Pub. No.: WO2006/124356
PCT Pub. Date: Nov. 23, 2006

(65) Prior Publication Data
US 2008/0213882 A1 Sep. 4, 2008

(51) Int. Cl.
*C12N 5/00* (2006.01)

(52) U.S. Cl. .......................................... 435/325

(58) Field of Classification Search ........................ None
See application file for complete search history.

(56) References Cited

U.S. PATENT DOCUMENTS

| 6,465,249 | B2 * | 10/2002 | Reya et al. ..................... 435/375 |
| 6,576,428 | B1 * | 6/2003 | Assenmacher et al. ........ 435/7.1 |
| 2002/0114772 | A1 | 8/2002 | Morgan et al. ............. 424/70.14 |

OTHER PUBLICATIONS

Ito Y et al. 2007. Isolation of murine hair-inducing cells using the cell surface marker prominin-1/CD133. J Invest Dermatol 127: 1052-60.*
Botchkarev VA et al. 2003. Molecular control of epithelial-mesenchymal interactions during hair follicle cycling. JID Symp Proc 8: 46-55.*
Baddoo M et al. 2003. Characterization of mesenchymal stem cells isolated from murine bone marrow by negative selection. J Cell Biochem 89: 1235-49.*
Bayer-Garner et al., "Syndecan-1 is strongly expressed in the anagen hair follicle outer root sheath and in the dermal papilla but expression diminishes with involution of the hair follicle", American Journal of Dermatopathology 2002 24(6):484-489.
Peterson et al., "Heparin II Domain of Fibronectin Uses α4β1 integrin to control focal adhesion and stress fiber formation, independent of syndecan-4", Journal of Biological Chemistry 2005 280 (8) :6915-6922.
Botchkarev et al., "Molecular Control of Epithelial-Mesenchymal Interactions During Hair Follicle Cycling", J. Investig. Dermatology Symp Proc. 2003 8:46-55.
Fernandez et al., "A dermal niche for multipotent adult skin-derived precursor cells", Nature Cell Biology 2004 22 (6):1082-1093.
Goding, Colin R., "Mitf from neural crest to melanoma:signal transduction and transcription in the melanocyte lineage", Genes & Development 2000 14:1712-1726.
Hardy, Margaret H., "The secret life of the hair follicle", Trends Genet. 1992 8:55-61.
Jahoda et al., "Induction of hair growth by implantation of cultured dermal papilla cells", Nature 1984 311:560-562.
Kishimoto et al., "Wnt signaling maintains the hair-inducing activity of the dermal papilla", Genes & Development 2000 14:1181-1185.
Meulemans et al., "Gene-Regulatory Interactions in Neural Crest Evolution and Development", Developmental Cell 2004 7:291-299.
Morris et al., "Capturing and profiling adult hair follicle stem cells", Nature Biotechnology 2004 22:411-417.
O'Shaughnessy et al., "The WNT Signalling Modulator, Wise, is Expressed in an Interactiobn-Dependent Manner During hair-Follicle Cycling", J Invest Dermatol 2004 123:613-621.
O'Shaughnessy et al., The role of BMP signalling in the control of ID3 expression in the hair follicle, Experimental Dermatology 2004 13:621-629.
Schmidt-Ullrich et al., "Molecular principles of hair follicle induction and morphogenesis", BioEssays 2005 27:247-261.
Sleeman et al., "Gene Expression in Rat Dermal Papilla Cells:Analysis of 2529 ESTs", Genomics 2000 69:214-224.
Tumbar et al., "Defining the Epithelial Stem Cell Niche in Skin", Science 2004 303:359-363.
Wilson et al., "The status of Wnt signalling regulates neural and epidermal fates in the chick embryo", Natures 2001 411:325-330.

* cited by examiner

*Primary Examiner* — Lora E. Barnhart Driscoll
(74) *Attorney, Agent, or Firm* — Licata & Tyrell P.C.

(57) ABSTRACT

The present invention relates to dermal papilla-specific markers and a method for isolating dermal papilla cells using the same. Dermal papilla cells isolated in accordance with the method of the invention and treated with BMP6 are useful for promoting hair growth.

1 Claim, No Drawings

METHOD FOR ISOLATING DERMAL PAPILLA CELLS AND USES THEREOF

INTRODUCTION

This invention was made with government support under Grant No. RO1 AR 31737 awarded by the National Institutes of Health. The U.S. government has certain rights in the invention.

BACKGROUND OF THE INVENTION

During embryogenesis, hair follicle formation is dependent upon a series of reciprocal interactions between the single-layered epithelium and a dermal cell condensate. This specialized cluster of mesenchymal cells becomes enveloped by the epithelial (matrix) cells at the base of the developing follicle, and postnatally, they persist as the dermal papilla (Hardy (1992)*Trends Genet.* 8:55-61; Schmidt-Ullrich and Paus (2005) *Bioessays* 27:247-261).

The architecture and biology of the mature follicle is complex. At the base, and in close association with the dermal papilla, matrix cells are transiently proliferative and maintain a relatively undifferentiated status. As matrix cells progress upward, they differentiate into the hair shaft (cortex and medulla) and the channel or inner root sheath that surrounds the hair. The inner root sheath is then encased by an outer root sheath contiguous with the epidermis. The entire structure is enclosed by a basement membrane composed of extracellular matrix proteins that separate the skin epithelium from dermis and dermal papilla. A small number of follicle melanocytes reside just above this membrane in the epithelial compartment of the hair bulb.

When matrix cells exhaust their proliferative capacity, the hair stops growing, and the lower epithelial part of the follicle enters a destructive phase (catagen). As the epithelium shrinks, the basement membrane and dermal papilla move upward. Following a resting period (telogen), epithelial stem cells at the base of the remaining hair follicle (the bulge) receive signals from the now adjacent dermal papilla and re-enter a growth phase (anagen) to regenerate the follicle and produce a new hair.

Genetic engineering has recently enabled the isolation of epithelial stem cells within the bulge (Tumbar, et al. (2004) *Science* 303:359-363; Morris, et al. (2004) *Nat. Biotechnol.* 22:411-417). When exposed to skin dermis, the descendants of a single epithelial stem cell can give rise to epidermis, follicles and sebaceous glands when engrafted onto the backs of Nude mice lacking hair (Blanpain, et al. (2004) *Cell* 118: 635-648). It has long been recognized that the critical dermal cells in this process are the dermal papilla (Hardy (1992) supra). In contrast to dermal (3T3) skin fibroblasts, which only permit epidermal repair in this assay, microdissected rat whisker dermal papilla cells induce hair growth (Jahoda, et al. (1984) *Nature* 311:560-562; Lichti, et al. (1993) *J. Invest. Dermatol.* 101:124S-129S). In vitro, the dermal papilla cells lose this ability. Co-culturing dermal papilla either with epidermal keratinocytes (Inamatsu, et al. (1998) *J. Invest. Dermatol.* 111:767-775) or with embryonic fibroblasts expressing a Wnt3a, but not a Sonic hedgehog transgene (Kishimoto, et al. (2000) *Genes Dev.* 14:1181-11), prolongs their potential. However, more recent studies suggest that Wnt3a on its own is not sufficient and that additional as yet unidentified factors are necessary for maintaining dermal papilla activity (Shimizu and Morgan (2004) *J. Invest. Dermatol.* 122:239-245).

A knowledge of the genes expressed by the dermal papilla and its neighbors would be of value in sifting through the complex mechanisms by which dermal papilla cells maintain their remarkable inductive function while in the niche and lose them outside of it. Most known dermal papilla markers have been found fortuitously. The relative inaccessibility of dermal papilla cells and/or their loss of potential in vitro have posed technical hurdles in isolating pure populations of these cells. Thus, although microarray and cDNA library analyses have been conducted on microdissected and/or cultured whisker dermal papillae (Sleeman, et al. (2000) *Genomics* 69:214-224; O'Shaughnessy, et al. (2004) *Exp. Dermatol.* 13:621-629; O'Shaughnessy, et al. (2004b) *J. Invest. Dermatol.* 123: 613-621), the array data have yielded only a handful of the known dermal papilla markers, making it difficult to evaluate the potential significance of unexpectedly expressed genes from these arrays.

A set of putative dermal papilla markers emerged when it was noted that cell aggregates cultured from whole skin dermis bear a resemblance to neurospheres cultured from neural crest cells (Fernandes, et al. (2004) *Nat. Cell Biol.* 6:1082-1093). Subsequent in vivo studies revealed that neural crest markers localized in the vicinity of dermal papilla, raising speculation those neural progenitor cells in the skin are derived from dermal papilla. These analogies were complicated by the close proximity of melanocytes (neural crest derived) and dermal papilla in the follicle, and by the fact that the parallels were largely drawn from identifying SKP markers in rodent whiskers. In contrast to other body sites, the entire head mesenchyme develops embryologically from neural crest (Le Douarin and Dupin (1993) *J. Neurobiol.* 24:146-161). These potential caveats aside, the existence of a population of multipotent neuroprogenitor cells in adult follicles would place the dermal papilla squarely at the center of significant clinical relevance. Accordingly, needed in the art are suitable markers for the identification and isolation of such cells. The present invention meets this long-felt need.

SUMMARY OF THE INVENTION

The present invention is a method for isolating a dermal papilla cell. The method involves the steps of obtaining a population of cells from a sample and sorting the population of cells based on the absence of CD34, CD45 and CD117 and the presence of a selected dermal papilla cell marker expressed by each cell. Isolated dermal papilla cells are lacking CD34, CD45 and CD117 and expressing a selected dermal papilla cell marker are also provided.

The present invention is also a method for promoting hair growth by contacting dermal papilla cells with an effective amount of BMP6 so that hair growth is promoted when said dermal papilla cells are contacted with skin cells.

DETAILED DESCRIPTION OF THE INVENTION

The present invention relates to a novel method for isolating dermal papilla cells using the absence of cell surface markers and the presence of at least one selected dermal papilla cell marker. Such selected dermal papilla cell markers are disclosed herein and provide a means to identify and isolate dermal papilla cells from non-dermal papilla cells in a skin sample. As BMP6 has now been found to enhance the hair inductive capacity of dermal papilla cells, the isolated dermal papilla cells can be pretreated with BMP6 and used to promote hair growth in skin.

Dermal papilla cells are underrepresented dermal residents that are centrally located and surrounded by a microenvironment composed of other cell types. Therefore, a novel strategy was devised that would enable the use of fluorescence-activated cell sorting to purify the dermal papilla from its complex cellular surroundings. Transgenic mice expressing RFP (red fluorescent protein) under the control of a Lef1 promoter fragment were engineered and mated to mice expressing histone H2BGFP under the control of a keratin 14 (K14) promoter fragment (Tumbar, et al. (2004) supra). In 4 day old (P4), double-transgenic skin, selective expression of cytoplasmic RFP was found in the dermal papilla, precortical/premedulla epithelial cells and melanocytes of the hair follicles. By contrast, nuclear H2BGFP was expressed most strongly in transiently amplifying cells of the basal epidermal layer, outer root sheath and bulge, but was also present in all skin epithelial cells.

To isolate follicles, P4 backskins were first treated with dispase to selectively remove and discard the epidermis and upper follicles, and then the dermal extracellular matrix was digested with collagenase. After trypsinization, the single cell suspension was subjected to three different FACS isolations, using channels specific for GFP and RFP in various combinations with antibodies against different cell surface markers. Five different populations of cells were purified: Outer root sheath ($GFP^{high}RFP^-$), matrix ($GFP^{low}RFP^-$), melanocytes ($RFP^{high}GFP^-CD117^+$), dermal papilla ($RFP^{high}GFP^-CD34^-CD45^-CD117^-$) and a dermal fraction enriched in fibroblasts ($RFP^-GFP^-CD34^-CD45^-CD117^-$).

The purity of each population was judged by immunofluorescence microscopy and RT-PCR analyses. The putative matrix fraction showed strong labeling with antibodies against proliferating nuclear antigen Ki67 and weak labeling with antibodies against K5 and K14. mRNAs in this population included Wnt10b, Msx2 and Foxn1, known to be expressed in matrix. By contrast, the putative outer root sheath fraction was strongly positive for K5 and β4 integrin, with reduced Ki67 and Msx2 and no detectable Wnt10b. Both dermal papilla and dermal fractions were enriched for vimentin, but only the dermal papilla fraction scored positive for mRNAs encoding the dermal papilla markers Alx4, Noggin (Nog), alkaline phosphatase (Akp2) and Fgf7. By contrast, the melanocytes fraction was positive for tyrosinase, Kit and melanophilin (Mlph). These data underscore the purity of the dermal papilla, not achieved by previous methods (Kishimoto, et al. (2000) supra; Shimizu, et al. (2004) supra; O'Shaughnessy, et al. (2004) supra; O'Shaughnessy, et al. (2004) supra; Sleeman, et al. (2000) supra).

The cell-cycle profiles of the five populations varied dramatically in accordance with the levels of anti-Ki67 labeling and 5-bromo-2'-deoxyuridine (BrdU) incorporation in vivo. Thus, whereas the quiescent dermal papilla and melanocytes populations displayed ~1% cells in S phase, the transiently dividing populations of matrix and outer root sheath showed ~15% of S phase cells. Taken together with the protein and mRNA expression patterns, the specificity of cell cycle profiles further indicated that the purification schemes were valid and confirmed the identity of each fraction.

By purifying all of the cell populations within the niche of the hair bulb, it was possible to obtain the transcriptional information necessary to dissect the commonalities and differences of these cell types both at a global and at a gene-by-gene basis. For each population, purification and microarray hybridizations (AFFYMETRIX® Moe430A) were performed in duplicate and >95% identity in array data was obtained. A cursory examination of the overall correlation of genes present in each fraction revealed the uniqueness of each cell population relative to the other cell types of the niche. While the correlation between replicates set the standard of a near-perfect match (r>0.96), there was a remarkably high correlation between the dermal papilla and dermal fraction, and the matrix and outer root sheath, respectively, highlighting the common mesenchymal origin of dermal papilla and dermal fraction and the close lineage relationship of matrix and outer root sheath. Unexpectedly, the lowest correlation occurred between dermal papilla and matrix, revealing striking differences between the two populations whose signaling exchange orchestrates the dynamics of the hair growth.

High-stringency comparative analyses was then conducted to uncover common and distinguishing features. More than two-thirds of the >22,000 probe-sets scored as present in at least one population, with the bulk of genes being present in at least 4, or all 5 fractions. Of these, ~6,000 probe-sets (4,000 genes) scored as present and unchanged in all fractions, providing a list of putative housekeeping or "molecular backbone" genes irrespective of the lineage or cell type. By contrast, only 150-300 genes scored as upregulated by at least two-fold in one fraction relative to the other four. In many cases, these genes were also selectively called present in only one of the fractions, indicative of a specialized function. These subsets provided "molecular signatures" for each population.

Each signature faithfully contained many of the previously assigned markers for each cell type and differentiation status (Goding (2000) *Genes Dev.* 14:1712-1728; Schmidt-Ullrich and Paus (2005) supra). In addition, the arrays permitted detailed comparisons of relative expression levels of these genes in different cell compartments (Table 1).

TABLE 1

| Dermal Papilla vs. Dermal Fraction ≧2x: 434 | | Matrix vs. Outer Root Sheath ≧2x: 270 | | Outer Root Sheath vs. Matrix ≧2x: 734 | | Melanocytes vs. Dermal Papilla ≧2x: 741 | |
|---|---|---|---|---|---|---|---|
| Fgf7 | 16x | Ovol1 | 6x | K15 | 14x | Mc1r | 14x |
| Akp2 | 12x | Kitl | 5x | Sfrp1 | 13x | Kit | 8x |
| Bmp4 | 12x | Lef1 | 4x | Tnc | 12x | Mlph | 8x |
| Fgfr1 | 4x | Bmp4 | 4x | Tcf3 | 5x | Tyr | 6x |
| Wnt5a | 4x | Msx1 | 4x | K14 | 4x | | |
| Ncam1 | 3x | Msx2 | 4x | Itga6 | 4x | | |
| Nog | 2x | Hoxc13 | 3x | Itgb1 | 3x | | |

The mRNA level for the matrix growth factor Fgf7 was >16× higher in dermal papilla than in the dermal fraction. mRNAs encoding known transcriptional regulators of matrix cell growth and differentiation were 4-6× higher in matrix than outer root sheath. Conversely, mRNAs encoding outer root sheath keratins were 3-15× higher in outer root sheath versus matrix. mRNAs required for melanin pigment granule production were 6-14× higher in melanocytes than dermal papilla.

The presence of cell type-preferred patterns of gene expression allowed for the identification of novel features of the signatures. Although the dermal fraction was used for comparative purposes, the four populations at the base of the follicle were concentrated on. Their signature genes and a list of common, unchanged genes (molecular backbone) were grouped into putative functional categories based upon established Gene Ontology classifications (see, e.g., geneontology.org on the world-wide web) and calculated significantly enriched categories. The common, unchanged group were largely genes encoding proteins involved in basic cellular functions, such as DNA, RNA and protein metabolism. In contrast, the differential and/or overlapping enrichment of genes in the specialized categories of the signatures provided a genomic level insight into the functional properties of the different niche cell types. Genes within the most relevant categories are listed in Table 2. An unexpected feature of the molecular signatures was the number of genes previously associated with hair disorders. In addition, the signatures contained novel genes associated with signal transduction pathways of hair follicle morphogenesis. These expression patterns will be useful in future studies aimed at understanding how these genes play functional roles in hair biology.

TABLE 2

| | Matrix | Outer Root Sheath | Dermal Papilla | Melanocytes |
|---|---|---|---|---|
| Cell Growth/Cancer | Cdkn1a<br>Cdkn2b<br>St14<br>Tob1<br>Psors1c2#<br>Ly6g6d<br>Bspry<br>S100A3<br>Tacstd2# | | S100A4(P)<br>S100b | Hlf |
| Signal Transduction | Notch1#<br>Notch3(P)<br>Rab25<br>Arhv<br>Map3k6<br>Shh<br>Tgfa#<br>Gprc5d<br>Prg<br>Bmp8a<br>Bmp2<br>Bmp4(P)<br>Bambi(P)<br>Wnt10a(P)<br>Wnt11<br>Wnt5A(P)<br>Wnt4(P)<br>Stra6<br>Axin2(P)<br>Kitl#<br>Tnfrsf19(P) | Inhbb<br>Sostdc1(P)<br>Wnt4(P)<br>Wnt10a(P)<br>Ptch(P)<br>Gpr49<br>Gpr56<br>PP1r14c<br>Ak4<br>Fgfbp1<br>Sh3md2<br>Rerg<br>Tnk1<br>Rasa1<br>Pthlh#<br>Il11ra1<br>Cxcl14<br>Ccl27 | a<br>Ptch#<br>Ptch2<br>Smo(P)<br>Hhip<br>Bcl2<br>Ctgf(P)<br>Crabp2<br>Crabp1<br>Pthrl#<br>Wnt5A<br>Wnt11(P)<br>Wif1<br>Sfrp1(P)<br>Sfrp2<br>Frzb<br>Fzd2(P)<br>Nkd2<br>Axin2(P)<br>Fgf7<br>Fgf10<br>Fgfr1#<br>Igfbp3<br>Pdgfra#<br>Bmp4#<br>Bmp6<br>Bmp7(P)<br>Nog#<br>Bambi(P)<br>Gdf10<br>Fst#<br>Grb14<br>Inhba<br>Sostdc1<br>Tgfbr1#<br>Igf1(P)<br>Ltbp1<br>Madh6(P)<br>Jak2<br>Stat5a<br>Stat5b | Kit<br>Gpr73<br>Gpr143<br>Rab27a<br>Rap2b<br>Rab20<br>Rab32<br>Npy<br>Dkk3<br>Nkd1<br>Nlk<br>Axin2<br>Wnt4<br>Wif1(P)<br>Irf4<br>Sgk3<br>Sbk<br>Mknk2<br>Mapk6<br>Ikbkb<br>Vegfb<br>Tnfrsf19 |
| Transcription/ Nuclear | Msx2#<br>Msx1#<br>Ovol1#<br>Hoxc13#<br>Dlx3#<br>Dlx2(P)<br>Gcl<br>Sox21<br>Lef1(P)#<br>Foxq1#<br>Foxn1#<br>Foxp1<br>Hod<br>Tcfcp2l2# | Bnc<br>Ets2<br>Tbx1<br>Vdr#<br>Egr2#<br>Hr(P)#<br>Irx5<br>Irx4<br>Irx2<br>Lmo1<br>Lhx2<br>Sox9<br>Runx1<br>Odz2 | Alx3<br>Meis1<br>Trps1#<br>Hoxc8<br>Hoxa9<br>Hoxa10<br>Sox18#<br>Sox2<br>Lef1(P)#<br>Tle2<br>Ctbp2<br>Shox2<br>Snai2<br>Twist1 | Lmo2<br>Pax3<br>AP2b<br>Sox6<br>Sox10<br>Tcf7<br>Lef1(P)<br>Etv5<br>Rarb<br>Klf5<br>Mdfi |
| | Sp6<br>Klf5<br>Idb1<br>Taf13<br>Nfe2l3<br>Cited4<br>Trps1(P)#<br>Hr(P)# | Nfib<br>HoxA1<br>Dlx2(P) | Cebpa<br>Pitx2<br>Prrx2<br>Pbx1<br>Idb2(P)<br>Ndr3(P)<br>Hey1<br>Gli2(P)#<br>Gli1(P) | |
| Cellular Junctions/ Cytoskeleton | Cldn4<br>Cldn10<br>Cldn1#<br>Ocln<br>Crb3<br>Pvrl4<br>Unc5b<br>Myo5b<br>Clic3<br>Gjb5<br>Gjb4<br>Dsc1<br>Gsdm#<br>Pstpip1<br>Krt1-24<br>Krt1-c29<br>Krt1-1<br>Krt1-5<br>Krt1-23<br>Krt1-2<br>Krt2-6g<br>Krt2-18<br>Krt2-10<br>Krtap8-1<br>Krtap15<br>Krtap3-3<br>Krtap16-3<br>Krtap14<br>Tuba4<br>Katna1<br>Calml3<br>Prom2 | Krt1-15#<br>Krt1-14#<br>Krt2-5#<br>Krt2-8<br>Enah<br>Farp1<br>Plek2<br>FHOS2<br>Jub<br>Myh8<br>Clca2<br>Gja1 | Ncam1<br>Vcam1<br>Itga9<br>Jam2<br>Cntn1<br>Dlgh3(P)<br>Tm4sf10<br>Epha7<br>Efnb3<br>Cdh11<br>Vim1(P) | Tubb3<br>Plxnc1<br>Myo7a<br>Myo5a<br>Tjp2<br>Igsf4<br>Igsf8 |
| Extracellular Matrix/Cell Adhesion | Tiam2 | Tnc<br>Col17a1#<br>Col4a5#<br>Gpc4<br>Col4a1(P)<br>Lamb3#<br>Lama5#<br>Lama3#<br>Agrn<br>Itgb6#<br>Itgb4#<br>Itga3#<br>Dst#<br>Sdc4<br>Sdc1<br>Sema3a<br>Plxnb2<br>Efemp1 | Col14a1<br>Col15a1<br>Lama2<br>Lamc3<br>Fbln2<br>Cspg2<br>Clstn2 | Plat |
| Neural Progenitor/ Neural | Sox9<br>Krox20<br>Sema3a<br>Nedd9<br>Crim1<br>Slc1a3 | Zic1<br>Zic3<br>Sox2<br>Prss12<br>Lrrn1<br>Enc1(P)<br>Gfra1<br>S100b<br>Robo1(P)<br>Fscn1<br>Snap91<br>Mdk<br>Enpp2<br>Ncam1<br>Snai2<br>Twist1<br>Ngfr(P)<br>Wnt5a | Tubb3<br>Sox10<br>Pax3<br>Npy<br>Cln2<br>Clsc6a8<br>Ptgds<br>Bmyc<br>Fabp7<br>C230021P08<br>Plp<br>Smpd1 | |

TABLE 2-continued

| Matrix | Outer Root Sheath | Dermal Papilla | Melanocytes |
|---|---|---|---|
| | | Shox2 | |
| | | Cspg2 | |
| | | Serpine2(P) | |

Each molecular signature was defined as the genes whose expression was upregulated by ≧2X in only one of the five P4 backskin cell populations. The gene abbreviations and/or accession numbers are according to the NCBI listings.
denote genes implicated in skin/hair disorders.
(P) denotes appreciable signal but high/higher in one of the other 4 populations.

The outer root sheath signature included genes encoding a complex array of largely unstudied putative skin transcription factors. This list contained known (Bcn, Ets2, Tcf3, Egr2/Krox-20, hairless/Hr and vitamin D receptor/VdR) as well as previously unrecognized outer root sheath transcription factors (Table 2). The signature was further distinguished by focal adhesion and extracellular matrix genes, reflecting an ability of outer root sheath cells to not only to adhere to, but also synthesize and remodel its adjacent basement membrane. Since extracellular matrix is composed of signaling molecules, the upregulation of these genes further indicated a possible feedback loop to reinforce cell-substratum contacts in the outer root sheath.

In contrast to outer root sheath, matrix cells are typified by their ability to respond to cues from their microenvironment and differentiate upward to form the six concentric rings of the hair follicle. The matrix signature revealed their status at the nexus of proliferation and differentiation (Table 2). In addition to established matrix transcription factors (Msx2, Msx1, Ovo1, Hoxc13, Dlx3, Foxn1, Hr, Lef1, AP-2), the signature included several forkhead cousins of Foxn1 (Nude mouse), one of which (Foxq1) has been linked to the Satin mutant mouse, defective in hair shaft differentiation (Hong, et al. (2001) *Genesis* 29:163-171). Also on this list were germ cell-less (gcl) and Tcfcp2l2 (grainyhead-like1), thought to function in early stem cell differentiation and/or lineage boundaries. The matrix signature also revealed a preponderance of genes encoding members of the Fgf, Wnt, Tgfβ, TGFα, Shh and Bmp signal transduction pathways (Table 2). This was in agreement with the established ability of matrix to orchestrate these signal transduction pathways and specify the hair shaft and its channel. Additionally, the signature included genes encoding keratins and other structural proteins. In part, this could reflect the early steps in lineage differentiation. However, for at least three of these structural genes, it is noteworthy that keratin c29 is highly homologous to K17 whose absence causes premature matrix apoptosis and alopecia in mice (McGowan, et al. (2002) *Genes Dev.* 16:1412-1422); skin lacking Cldn1 (claudin 1) displays abnormally short hairs (Furuse, et al. (2002) *J. Cell Diol.* 156:1099-1111), and Gsdm (gasdermin) mutations have recently been linked to alopecia in mice (Runkel, et al. (2004) *Genomics* 84:824-835).

Novel features of the dermal papilla were identified that may give insight into understanding how these cells exert their power over epithelial stem cells and their outer root sheath and matrix progeny. By comparing against dermal fraction, general fibroblast features were screened out, e.g., expression of type I and type III procollagen chains, vimentin, and TGFβ1-induced genes. By contrasting the dermal papilla with outer root sheath and matrix signatures, genes exclusively expressed in either compartment could be identified and predictions could be made regarding the epithelial-mesenchymal crosstalk that transpires in the hair bulb.

The purity of the dermal papilla cells provided herein yielded an unprecedented sensitivity of detection. Of approximately 30 genes reported to be expressed in dermal papilla in vivo (Botchkarev and Kishimoto (2003) *J. Investig. Dermatol. Symp. Proc.* 8:46-55), 24 were either in the dermal papilla signature disclosed herein or expressed in dermal papilla but more abundant in one or more of the other populations. By contrast, only 3 had appeared on a prior array list from microdissected dermal papilla (O'Shaughnessy, et al. (2004) supra) and only 5 were on a list of 309 expressed genes from cultured dermal papilla (Sleeman, et al. (2000) supra). Most of the ~180 genes in the dermal papilla signature disclosed herein encoded novel factors involved in transcription, cell communication and signaling. Unexpectedly, less than 5% of these dermal papilla signature genes appeared on the arrays of microdissected whisker dermal papilla in vivo (O'Shaughnessy, et al. (2004) supra) or in vitro (Sleeman, et al. (2000) supra).

Given the near-complete lack of overlap between the presently disclosed dermal papilla signature and prior published reports, it was important to verify the novel aspects of each signature, as had already been done for the well-established features. Semi-quantitative PCR confirmed that the majority of genes were expressed predominantly by only a single cell population, i.e., the hallmark of the signature lists. The few exceptions were readily explained upon inspection of the gene expression profiles across the 5 populations. For example, follistatin (Fst) and Sostdc1 (ectodin/wise) scored as ~3× higher in dermal papilla than in outer root sheath, but 3-100× higher in outer root sheath than in the other 3 fractions. Analogously, Wnt5a and the Gata 3-like factor Trps1 (tricho-rhino-phalangeal syndrome1) scored as ~3-7× higher in dermal papilla than in matrix, but 1.5-35× higher in matrix than in other fractions.

Further, it was shown that expression of the dermal papilla signature genes could be detected in highly enriched pelage follicle preparations. For a number of novel dermal papilla genes, in situ hybridization and immunofluorescence were employed to verify mRNA expression patterns and extend these findings to the protein level. That the dermal papilla signature bears strong resemblance to the list of known dermal papilla genes and bears little or no resemblance to previously published profiles of dermal papilla cells, emphasizes the importance of conducting array analyses on purified populations of skin dermal papilla cells. The PCR, in situ hybridization and immunofluorescence data offer strong evidence as to the faithfulness and reliability of the signatures, and provide the first clear view of the dermal papilla and its niche microenvironment.

Subsequently, the physiological relevance of the dermal papilla signature was analyzed. In this regard, the dermal papilla signature contained a number of genes previously linked to hair disorders, but poorly understood in terms of expression and function. These included Trps1, Sox18, Fst and activinβ-A (Inhba) (Brown, et al. (2000) *Nat. Genet.* 25:453-457; James, et al. (2003) *Genesis* 36:1-6; Jhaveri, et al. (1998) *Mol. Cell. Neurosci.* 12:206-219; Momeni, et al. (2000) *Nat. Genet.* 24:71-74). Of additional note was the dermal papilla signature gene Fgf10, shown recently to be required for embryonic whisker development (Ohuchi, et al. (2003) *Diochim. Biophys. Res. Commun.* 302:562-567). Fgf10 and Fgf7 bind to the same receptor (encoded by Fgfr2 and in the matrix signature), and Fgf10's presence in the dermal papilla signature explains why Fgf7 knockout mice display a milder hair phenotype than the conditional Fgfr2 knockout (De Moerlooze, et al. (2000) *Development* 127: 483-492; Guo, et al. (1996) *Genes Dev.* 10: 165-175).

Further insights into the dermal papilla-matrix crosstalk came from evaluating the distribution of Shh pathway members. Whereas Shh is expressed by matrix, Shh receptor and downstream effector genes were part of dermal papilla's signature. Additionally, mRNA encoding hedgehog-interacting inhibitory protein (Hhip), was >80> higher in dermal papilla than matrix. By in situ hybridization and anti-Hhip immunofluorescence, Hhip was detected at the early stages of follicle downgrowth. This was of interest because in lung development, Shh signaling through Patched can accentuate Hhip expression, making the extending lung bud tip refractory to Shh signaling and permissive for Fgf10 expression (Chuang, et al. (2003) *Genes Dev.* 17:342-347). Moreover, Fgf10 is known to be negatively regulated by Shh, and conversely, both mesenchymal Fgf10 and also the BMP inhibitor Noggin can enhance epithelial Shh expression (Botchkarev, et al. (1999) *Nat. Cell Biol.* 1:158-164; Rice, et al. (2004) *J. Clin. Invest.* 113:1692-1700). When taken together, these findings indicate a regulatory circuitry for sustaining expression of Fgf10/7 in Hhip-positive dermal papilla and permitting Shh in matrix. Since excess Shh would be expected to override the effects of Hhip and downregulate Fgf10 and Fgf7, this may also explain why Shh treatment per se did not maintain the inductive ability of cultured dermal papilla (Kishimoto, et al. (2000) supra).

Given the reported effects of Wnts on the maintenance of dermal papilla potential (Kishimoto, et al. (2000) supra; Shimizu and Morgan (2004) supra) and the presence of Wnt5a in embryonic hair placodes (Reddy, et al. (2001) *Mech. Dev.* 107:69-82), it was of interest that Wnt5a and possible Wnt effector genes were in the dermal papilla signature. However, the list also included genes encoding secreted Wnt inhibitors (Wif1, Sfrp2 and Frzb). Semi-quantitative RT-PCR and anti-Wif1 immunofluorescence supported these observations. Like Hhip, Wif1 expression was maintained in adult dermal papilla and present at different stages of the hair cycle.

The number of BMP pathway members whose mRNA expression levels were upregulated by at least 2× in dermal papilla was unexpected. BMP4 has already been implicated in the cross-talk that specifies hair differentiation (Botchkarev (2003) *J. Invest. Dermatol.* 120:36-47). BMP6 was notable in that its mRNA levels were >10× higher in dermal papilla than the four other populations, a feature confirmed by in situ hybridization. All the cells within the hair bulb, including the dermal papilla, expressed the requisite BMP receptor (Bmpr1a). This said, the dermal papilla signature included an unexpected number of genes encoding BMP inhibitors such as Noggin, Gdf10, Sostdc1/Ectodin/Wise (O'Shaughnessy, et al. (2004) supra), Prdc (protein related to Dan/Cerberus) and Bambi. The possible role of BMPs/BMP inhibitors in promoting dermal papilla character has not been appreciated.

It has been reported that skin cultures contain neurosphere-like structures that can be induced to form neurons and glial cells (Fernandes, et al. (2004) *Nat. Cell Biol.* 6:1082-1093; Toma, et al. (2001) *Nat. Cell Biol.* 3:778-784). Although prior array data on dissected whisker dermal papilla and their cultures showed no resemblance of dermal papilla to neurally-derived cells (O'Shaughnessy, et al. (2004) supra; Sleeman, et al. (2000) supra), several markers expressed by the skin-derived neurospheres were traced by in situ hybridization to whisker follicles (Fernandes, et al. (2004) supra). The relative lack of resemblance between these prior whisker "dermal papilla" screens and the instant signature containing bona fide dermal papilla markers offered a possible explanation for these discrepancies. However, since head mesenchyme in its entirety is derived from neural crest, a documented resemblance between whisker dermal papilla and neural progenitor cells would not be unexpected. The instant array data allowed for the determination of whether SKPs and/or neural progenitors share similarities with dermal papilla from skin whose mesenchyme is not derived from neural crest and whether dermal papilla character compares to that of neural progenitors, nearby melanocytes (of known neural crest origin), and dermal fibroblasts (derived from dermamyotome).

Initially, the relation between the neurosphere-like structures (SKPs) cultured from skin dermis was examined (Fernandes, et al. (2004) supra). Only 5 genes, Snai2 (slug), Twist1, Cspg2 (versican), Nexin1 and Ncam1, have been reported to be expressed in both SKPs and backskin follicles (Kishimoto, et al. (2000) supra; Fernandes, et al. (2004) supra; Muller-Rover, et al. (1998) *J. Histochem. Cytochem.* 46:1401-1410; Yu, et al. (1995) *J. Cell Sci.* 108(Pt12):3867-3874). Four of these genes appeared on the instant dermal papilla signature. Of the remaining known SKP-expressed genes (Shox2, Pax3, Snail1, Sox9, Nestin, Wnt-1, Sca-1/Ly6A-E, Twist2 and Fn1) (Fernandes, et al. (2004) supra), only Shox2 was in the dermal papilla signature, and only Fn1 scored as present in dermal papilla. Conversely, Sox2 and Ngfr (p75) were readily detected in pelage dermal papilla and yet they were reported as absent in SKPs (Fernandes, et al. (2004) supra).

Although differences between SKP cultures and in vivo dermal papilla expression patterns had escaped prior notice, such differences could nevertheless exist because SKPs are derived from cultures rather than a purified in vivo cell population. Therefore, the broader relation between dermal papilla and neural stem cells was addressed. In this regard, it was notable that Zic1, Zic3 and Sox2 were all part of the dermal papilla signature and absent in melanocytes. These mRNAs encode key transcription factors that specify neuronal fate at the expense of ectoderm (Huang and Saint-Jeannet (2004) *Dev. Biol.* 275:1-11; Meulemans and Bronner-Fraser (2004) *Dev. Cell* 7:291-299. The signature also included ~10 other neural genes.

The preferred expression of these genes in dermal papilla was confirmed by using semi-quantitative RT-PCR. Most genes were preferentially upregulated in dermal papilla fraction relative to all of the other fractions, including melanocytes. An exception was Sox10, whose expression by array analyses and by RT-PCR scored as preferentially expressed in melanocytes. Also confirming the array data were RT-PCR analyses of Sox9, which scored as preferentially expressed in the outer root sheath, and Wnt5a, which scored as present in matrix and dermal fraction populations as well as in the dermal papilla. Dermal papilla localization of Prss12, glial derived neurotrophic factor receptori (Gfra1) and Midkine (Mdk) was also confirmed by in situ hybridization. Co-labeling with anti-tyrosinase (melanocytes-specific) verified that the hybridization was in the dermal papilla and not melanocytes compartment. In addition, the expression of these and additional neuronal/neural crest-related dermal papilla signature genes was verified in highly purified follicle preparations. Further, spontaneous neuronal/glial differentiation was observed in passaged dermal papilla cell cultures at low frequency and some of these neuronal-like cells still exhibited dermal papilla characteristics, as judged by alkaline phosphatase staining.

Despite these unanticipated parallels between backskin dermal papilla and cells of neural origin, the dermal papilla signature did not strongly resemble neural crest, neural stem cells or any of the neural lineages described to date, including melanocytes. Additionally, and equally unexpected, the dermal papilla signature was also distinct from the backskin dermal fibroblast signature. Taken together, these data point to a signature unique to the dermal papilla and not shared by any of the cell populations constituting the distinctive dermal papilla niche microenvironment.

Additional analysis was conducted to identify features of the dermal papilla microenvironment that impact dermal papilla gene expression and function. BMP signaling was primarily analyzed. BMP signaling was prominently featured in the dermal papilla and matrix arrays and is known to regulate expression of the neural specifiers (Sox2, Zic1/3) which were part of the dermal papilla signature (Wilson, et al. (2001) Nature 411:325-330; Meulemans and Bronner-Fraser (2004) supra). When taken together with the evidence for both positive and negative roles of BMP signaling in hair follicle morphogenesis (Botchkarev (2003) supra; Schmidt-Ullrich and Paus (2005) supra), these findings indicated that BMPs may have a positive or negative influence on the dermal papilla signature. BMP6 was evaluated as its mRNA was expressed >10× higher in dermal papilla than any other cell type examined.

Although cultured dermal papilla cells retained expression of many of their signature genes, a number of notable dermal papilla markers, including Noggin, were lost upon culture. All but three were restored upon BMP6 addition to the cultures. Moreover, of the signature genes examined, only 13mp6 mRNA itself appeared to be markedly downregulated in the presence of BMP6. The persistence of Sox2 and Zic1/3 in BMP-treated dermal papilla cultures was unexpected, give that BMPs repress these genes in developing neurons at the neural plate (Muelemans and Bronner-Fraser (2004) supra).

Anti-Alx4 immunofluorescence and alkaline phosphatase activity revealed a dose-dependent and broad impact of BMP6 throughout the dermal papilla cell cultures. The BMP6-mediated differences in gene expression were manifested early during passage, and at times when no major differences in cell proliferation were noted. Real time (RT)-PCR analysis was carried out to conduct more quantitative and comparative analyses with a number of key genes (i.e., Akp2, Alx4, Wif1, Nog, Hey1, and Bmp6). The responsiveness of dermal papilla cells to BMP6 appeared to be dependent upon certain intrinsic properties, as they were not observed with 3T3 dermal skin fibroblasts.

The dermal papilla response to BMP6 was also observed to a lesser extent with BMP4, but it was not seen with a number of other growth factors, notably Shh and Wnt3A. Moreover, the positive outcomes of BMP6 and BMP4 on dermal papilla gene expression were thwarted by exogenous Noggin, attributing these effects specifically to the recombinant BMPs, and not a contaminant. BMP6 treatment resulted not only in a downregulation of Bmp6 mRNAs, but also in a dose-dependent upregulation of Noggin mRNAs, uncovering a feedback regulatory loop between BMP activators and inhibitors.

This data indicated that dermal papilla gene expression in vitro more closely mimicked the in vivo pattern when exposed to BMPs rather than BMP inhibitors. This was further supported by anti-pSmad1 immunofluorescence, which recognizes the activated (phosphorylated) transcription factor downstream from BMP receptor signaling. BMP6 treatment resulted in nearly a 10× increase in pSmad1 positive nuclei in dermal papilla cultures. Anti-pSmad1 also labeled the hair follicle bulb in vivo. Anti-tyrosinase immunofluorescence of serial sections revealed that melanocytes exhibited the strongest anti-pSmad1 labeling in the hair bulb. A gradient of anti-pSmad1 labeling was observed within the dermal papilla, indicating that the level of BMP signaling may be greater in the upper dermal papilla than at the base of the hair bulb.

When grafted onto the backs of Nude mice, epidermal keratinocytes can reepithelialize a wound but are not able to generate hair follicles, even when grafted with cultured 3T3 dermal fibroblasts or passaged dermal papilla cells (Lichti, et al. (1993) supra; Kishimoto, et al. (2000) supra). This system was employed to address whether BMP6 treatment could enhance the ability of cultured dermal papilla cells to promote hair follicle formation in vivo.

Epidermal keratinocytes were isolated from newborn K14-GFPactin mice and grafted into areas where the full-thickness skin of Nude mice had been removed. GFP-positive keratinocytes provided a covering to the wound site but no hairs developed. Without underlying support from dermal fibroblasts, the epidermal graft was very thin and it contracted, as observed previously (Lichti, et al. (1993) supra). In contrast, when grafts not only contained epidermal keratinocytes, but also the cultured descendants from FACS-isolated dermal papilla cells, signs of hair formation and reepithelialization were observed, with minimal contraction of the graft. When grafts contained dermal papilla cells that had been exposed to 200 ng/mL BMP6 in culture, the results were even more dramatic. Although limitations in the grafting procedures resulted in some variability among individual experiments, when averaged over six experiments, BMP6 consistently showed an enhanced effect in promoting hair growth.

Further analyses of grafted skins revealed contributions of the GFP-positive keratinocytes to the epidermis, sebaceous glands and hair follicles. The angling and spacing of hair follicles was aberrant, and consequently it was difficult to obtain saggittal sections through the follicle plane. This said, extensive sectioning and staining with biochemical markers revealed a normal morphology and differentiation program. Further, follicles displayed what appeared to be a normal dermal papilla at their base. These dermal papilla cells labeled with antibodies against a number of dermal papilla markers and were positive for alkaline phosphatase activity.

A sharp boundary existed between the host and grafted skin with regards to the presence of follicles and alkaline phosphatase-positive dermal papilla. To further monitor the graft boundaries and the origins of dermal cells within the graft, cells from male mice were used to graft to female nude mice. Fluorescence in situ hybridization (FISH) immunofluorescence microscopy revealed the presence of Y-chromosome-positive, alkaline phosphatase-positive dermal papilla cells, consistent with their parental origin. Moreover, the dermal fibroblasts also contained Y chromosome positive cells. Y-FISH positive dermal fraction cells were not seen in either the host skin or KC control skin. Conversely, in analogous engraftments with dermal fraction cells, functional dermal papilla were not generated (Lichti, et al. (1993) supra). Together, these findings demonstrate that under the conditions used here, BMP6 treated dermal papilla cultures not only maintained follicle-inducing capabilities, but also adopted at least one alternative lineage.

Having demonstrated that dermal papilla cells can be readily isolated and distinguished from surrounding populations of cells, the present invention is a method for isolating a dermal papilla cell based on the absence of CD34, CD45 and CD117 and the presence of a selected dermal papilla cell marker expressed by each cell. As used herein, a selected dermal papilla cell marker is intended as a marker which has been shown herein to be expressed only in a dermal papilla cell and not in matrix, outer root sheath or keratinocyte cells. Such selected dermal papilla cell markers are listed in Table 3.

TABLE 3

| Category | Gene Designation | Entrez GeneID No. |
|---|---|---|
| Cell Growth/Cancer | S100A4 | 20198 |
| | S100b | 20203 |
| Signal Transduction | a | 50518 |
| | Ptch | 19206 |
| | Ptch2 | 19207 |
| | Smo | 319757 |
| | Hhip | 15245 |
| | Bcl2 | 12043 |
| | Ctgf | 14219 |
| | Crabp2 | 12904 |
| | Crabp1 | 12903 |
| | Pthr1 | 19228 |
| | Wnt5a | 22418 |
| | Wnt11 | 22411 |
| | Wif1 | 24117 |
| | Sfrp1 | 20377 |
| | Sfrp2 | 20319 |
| | Frzb | 20378 |
| | Fzd2 | BB371406* |
| | Nkd2 | 72293 |
| | Axin2 | 12006 |
| | Fgf7 | 14178 |
| | Fgf10 | 14165 |
| | Fgfr1 | 14182 |
| | Igfbp3 | AV175389* |
| | Pdgfra | 18595 |
| | Bmp4 | 12159 |
| | Bmp6 | NM_007556* |
| | Bmp7 | 12162 |
| | Nog | 18121 |
| | Bambi | 68010 |
| | Gdf10 | 14560 |
| | Fst | 14313 |
| | Grb14 | 50915 |
| | Inhba | 16323 |
| | Sostdc1 | 66042 |
| | Tgfbr1 | 21812 |
| | Igf1 | 16000 |
| | Ltbp1 | 268977 |
| | Madh6 | AF010133* |
| | Jak2 | 16452 |
| | Stat5a | 20850 |
| | Stat5b | 20851 |
| Transcription/Nuclear | Alx3 | 11694 |
| | Meis1 | 17268 |
| | Trps1 | 83925 |
| | Hoxc8 | 15426 |
| | Hoxa9 | 15405 |
| | Hoxa10 | 15395 |
| | Sox18 | 20672 |
| | Sox2 | 20674 |
| | Lef1 | 16842 |
| | Tle2 | 21886 |
| | Ctbp2 | 13017 |
| | Shox2 | 20429 |
| | Snai2 | 20583 |
| | Twist1 | 22160 |
| | Cebpa | BC01118* |
| | Pitx2 | 18741 |
| | Prrx2 | 20204 |
| | Pbx1 | 18514 |
| | Idb2 | 15902 |
| | Ndr3 | 29812 |
| | Hey1 | 15213 |
| | Gli2 | 14633 |
| | Gli1 | 14632 |
| Cellular Junctions/ Cytoskeleton | Ncam1 | BB698413* |
| | Vcam1 | 22329 |
| | Itga9 | 104099 |
| | Jam2 | 67374 |
| | Cntn1 | 12805 |
| | Dlgh3(P) | 53310 |
| | Tm4sf10 | 192216 |
| | EphA7 | 13841 |
| | Efnb3 | 13643 |
| | Cdh11 | 12552 |
| | Vim1(P) | 22352 |
| Extracellular Matrix/Cell Adhesion | Col14a1 | 12818 |
| | Col15a1 | 12819 |
| | Lama2 | 16773 |
| | Lamc3 | 23928 |
| | Fbln2 | 14115 |
| | Cspg2 | 13003 |
| | Clstn2 | 64085 |
| Neural Progenitor/ Neural | Zic1 | 22771 |
| | Zic3 | 22773 |
| | Sox2 | 20674 |
| | Prss12 | 19142 |
| | Lrrn1 | 16979 |
| | Enc1 | 13803 |
| | Gfra1 | 14585 |
| | S100b | 20203 |
| | Robo1 | 19876 |
| | Fscn1 | 14086 |
| | Snap91 | 20616 |
| | Mdk | 17242 |
| | Enpp2 | 18606 |
| | Ncam1 | BB698413* |
| | Snai2 | 20583 |
| | Twist1 | 22160 |
| | Ngfr | BB151515* |
| | Wnt5a | 22418 |
| | Shox2 | 20429 |
| | Cspg2 | 13003 |
| | Serpine2 | 20720 |

*Indicates Representative Public ID No.

To facilitate isolation of a dermal papilla cell, it is desirable to use one or more cell surface-localized, selected dermal papilla cell markers such as the novel receptors provided in Table 3 (i.e., Ptch2, Hhip, Frzb, Pdgfra, Tgfbr1, Ncam1, Vcam1, Itga9, Epha7, Efnb3, Ngfr). Alternatively, a dermal papilla cell can be isolated based solely on the presence of one or more selected dermal papilla cell markers, i.e., without sorting based on the absence of CD34, CD45 and CD117. In one embodiment, a dermal papilla cell is isolated based on the presence of Hhip, Frzb, Pdgfra, Tgfbr1, Vcam1, Itga9, Epha7, or Efnb3. As used herein, a sample is intended to include skin tissue. Methods for obtaining a population of cells from skin samples are described herein and elsewhere and are well-established in the art.

In general, the step of sorting the population of cells into dermal papilla and non-dermal papilla cells can be carried out using cell-sorting methods such as immunopanning, FACS, and magnetically labeled beads. Such methods are generally carried out using a binding agent, such as a fluorescently labeled antibody or ligand, which specifically binds to the surface-localized cell marker of interest thereby facilitating sorting of cells expressing said surface-localized cell marker from cells which do not express the marker. For example, CD34, CD45 and CD117 antibodies which can be used to sort non-dermal papilla cells from dermal papilla cells can be obtained from commercial sources such as ABCAM® (Cambridge, Mass.), BD Biosciences, and Research Diagnostics, Inc. (Flanders, N.J.). Likewise, labeled antibodies which bind to selected dermal papilla cell markers may be obtained from commercial sources. Alternatively, antibodies to a particular selected dermal papilla cell marker can be generated using classical cloning and cell fusion techniques well-known to the skilled artisan (see, e.g., Kohler and Milstein (1975) *Nature* 256:495-497; Harlow and Lane (1988) Antibodies: A Laboratory Manual, Cold Spring Harbor Laboratory, New York) phage display methods (see, e.g., Huse, et al. (1989) *Science* 246(4935):1275-81).

Alternatively, sorting can be carried out by magnetic separation employing, e.g., systems such as MACS® (Miltenyi Biotec, Auburn, Calif.) and BIOMAG® Anti-CD34 antibodies (Polysciences, Inc., Warrington, Pa.).

Once sorted, the purity of the dermal papilla cells can be determined by identifying the presence of one or more of the markers selectively expressed in dermal papilla and the absence of one or more of the markers selectively expressed in neighboring matrix, root sheath, or keratinocyte cells (see Table 2). Detection of these markers can be carried out using any standard method for detecting a protein or mRNA sequence. For example, proteins can be detected by contacting a cell with a binding agent (e.g., an antibody or aptamer) which binds the marker and detecting binding agent complexes using standard assays (e.g., an immunoassay). When the binding agent is, for example, a peptide aptamer, the binding agent-antigen complex can be directly detected by, for example, a detectable marker protein (e.g., β-galactosidase, GFP or luciferase) fused to the aptamer.

Alternatively, expression of the marker is detected via the of presence the marker mRNA using methods such as northern blot analysis, reverse-transcriptase PCR, microarray analysis and the like. Due to the ease of use, it is generally desirable to detect the mRNA sequences using a PCR-based approach. In general, this involves contacting a cell sample with two or more PCR primers which specifically hybridize with nucleic acids encoding the marker of interest or which flank the coding region of the marker of interest, subjecting the sample to multiple steps of PCR amplification and detecting the presence or absence of the amplified sequence (e.g., using gel analysis, blotting methods, or fluorescently-labeled primers). Alternatively, an oligonucleotide, an aptamer, a cDNA, an antibody, or a fragment thereof, which interacts with at least a portion of the nucleic acid sequence encoding the marker of interest is configured in an array on a chip or wafer and used for detecting nucleic acids encoding the marker. Primers or oligonucleotides can be selected from any region of the locus encoding the marker and generally specifically anneal and amplify at least a portion of nucleic acid encoding the marker and no other nucleic acid. In general, the primers are 12 to 30 bp in length and generate a PCR amplicon of 50, 100, 200 400, 600, 1000 bp or more in length. The fundamentals of non-degenerate PCR are well-known to the skilled artisan, see, e.g. McPherson, et al., PCR, A Practical Approach, IRL Press, Oxford, Eng. (1991).

The method of the present invention is particularly useful in isolating dermal papilla cells of mammalian origin (e.g., human, mice, rats, pigs, cows, dogs, and the like). In addition, it is contemplated that the dermal papilla cells isolated in accordance with the methods of the invention would be useful in human tissue culture systems. Advantageously, using the sorting method disclosed herein a single, individual dermal papilla cell can be isolated and cultured under appropriate conditions to generate a clonal population of cells expressing markers specific to the dermal papilla cell and exhibiting the characteristics of inducing de novo hair growth in developing embryonic epidermis as well as to induce a new hair cycle in conjunction with bulge epithelial stem cells.

Dermal papilla cells isolated and maintained in accordance with the methods disclosed herein are contemplated as being useful in tissue regeneration and repair (e.g., hair growth) by grafting said cells to an animal in need of treatment, the treatment of a broad range of diseases, and basic research to understand the properties of dermal papilla cells and their ability to induce hair growth.

The present invention is also a method for promoting hair growth by contacting dermal papilla cells with an effective amount of BMP6 so that hair growth is promoted when the BMP6-treated dermal papilla cells are contacted with skin cells (e.g., human skin, a skin graft, or isolated keratinocytes). Dermal papilla cells exposed to an effective amount of BMP6 have enhanced hair inductive capacity compared to dermal papilla cells not contacted with BMP6. Suitable amounts of BMP6 which enhance hair induction can be in the range of 5 to 500 ng/mL or more desirably 100 to 300 ng/mL. BMP6 can be provided to the dermal papilla cells in the form of a purified polypeptide or as a BMP6 nucleic acid suitable for expression in the dermal papilla cells.

A suitable form for expression provides that the BMP6 nucleic acid includes one or more regulatory sequences operatively-linked to BMP6 coding sequence in a manner which allows for transcription of the nucleic acids into mRNA and translation of the MRNA into the protein. Regulatory sequences can include promoters, enhancers and other expression control elements (e.g., polyadenylation signals). Such regulatory sequences are known to those skilled in the art and are described in Goeddel D. D., ed., Gene Expression Technology, Academic Press, San Diego, Calif. (1991).

BMP6 can be directly delivered as a naked DNA construct to dermal papilla cells using mechanical methods, such as microinjection, liposome-mediated transfection, electroporation, or calcium phosphate precipitation. Alternatively, a naked DNA construct encoding BMP6 can be combined with a condensing agent, such as polylysine, polyarginine, polyornithine, protamine, spermine, spermidine, or putrescine, to form a gene delivery vehicle. Many suitable methods for making such linkages are known in the art. Alternatively, a construct encoding BMP6 can be associated with a liposome for delivery to a dermal papilla cell. Other suitable methods of providing such constructs include DNA-ligand combinations or microbubble ultrasound transduction (Lu, et al. (2003) *Gene Ther.* 10(5):396-405).

As an alternative to directly introducing a BMP6 DNA construct into a dermal papilla cell, the BMP6 nucleic acid can be incorporated into a viral vector for delivery to the target cells. Vectors, such as replication-defective retroviruses, adenoviruses and adeno-associated viruses can be used. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well-known to those skilled in the art. Examples of suitable packaging virus lines include ψCrip, ψCre, ψ2 and ψAm. The genome of adenovirus can be manipulated such that it encodes and expresses a polypeptide of the invention but is inactivated in terms of its ability to replicate in a normal lytic viral life cycle (Berkner, et al. (1988) *BioTechniques* 6:616; Rosenfeld, et al. (1991) *Science* 252:431-434; Rosenfeld, et al. (1992) *Cell* 68:143-155). Suitable adenoviral vectors derived from the adenovirus strain Ad type 5 dl324 or other strains of adenovirus (e.g., Ad2, Ad3, Ad7 etc.) are well-known to those skilled in the art. In vivo use of adenoviral vectors is described in Flotte, et al. ((1993) *Proc. Natl Acad. Sci.* 90:10613-10617) and Kaplitt, et al. ((1994) *Nature Genet.* 8:148-153). Other viral vectors, such as those based on togaviruses or alpha viruses, can also be employed. Alternatively, an adeno-associated virus vector such as that disclosed by Tratschin, et al. ((1985) *Mol. Cell. Biol.* 5:3251-3260) may be used to express a BMP6 polypeptide.

Expression of BMP6 in dermal papilla cells can be monitored by detecting production of BMP6 mRNA or by detecting the BMP6 protein product using, for example, immunological techniques.

In a particular embodiment, BMP6 is provided as a purified BMP6 polypeptide or active fragment thereof. As will be appreciated by the skilled artisan, a purified BMP6 polypeptide can be either recombinantly-produced or chemically-synthesized.

In general, recombinant production of BMP6 requires incorporation of nucleic acids encoding BMP6 (e.g., see GENBANK Accession No. NM_001718; Celeste, et al. (1990) *Proc. Natl. Acad. Sci. USA* 87(24):9843-7) into a recombinant expression vector in a form suitable for expression of the protein in a host cell. It should be understood that the design of the expression vector can depend on the host cell being transformed (e.g., eukaryotic vs. prokaryotic) and the level of expression required. The production of recombinant DNA, vectors, host cells, and proteins by genetic engineering techniques is well-known. See, e.g., U.S. Pat. No. 4,761,371; U.S. Pat. No. 4,877,729; U.S. Pat. No. 4,912,038; and U.S. Pat. No. 4,879,224 and Sambrook and Russell (2001) In: Molecular Cloning, a Laboratory Manual, Cold Spring Harbor Laboratory; 3rd edition. Suitable vectors for recombinant protein expression in mammalian, yeast, or prokaryotic systems are commercially available from such sources as STRATAGENE®, INVITROGEN™, Pharmacia and the like. Many of these vectors encode heterologous polypeptides, i.e., signal sequences for secretion and/or other polypeptide which aid in the purification of the protein of interest. Desirably, the heterologous polypeptide has a specific cleavage site to remove the heterologous polypeptide from the protein of interest. Other useful heterologous polypeptides which can be fused to the protein of interest are those which increase expression or solubility of the fusion protein or aid in the purification of the fusion protein by acting as a ligand in affinity purification. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse GST, maltose E binding protein, or protein A, respectively, to the protein of interest.

Once produced, BMP6 can be recovered from culture medium as a secreted polypeptide, although it also may be recovered from host cell lysates when directly expressed without a secretory signal. When BMP6 is expressed in a recombinant cell other than one of mammalian origin, the polypeptide is substantially free of proteins or polypeptides of mammalian origin. However, it may be necessary to purify BMP6 from recombinant cell proteins using conventional protein purification methods to obtain preparations that are substantially homogeneous as to BMP6. As a first step, the culture medium or lysate is centrifuged to remove particulate cell debris. The membrane and soluble protein fractions are then separated. The recombinant BMP6 protein can then be purified from the soluble protein fraction. The recombinant BMP6 protein thereafter is purified from contaminant soluble proteins and polypeptides using any of the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX® G-75; and ligand affinity chromatography.

In addition to recombinant production, BMP6 can be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer, Boston, Mass.). Various fragments of the polypeptide can be chemically-synthesized separately and combined using chemical methods to produce a full-length molecule.

Whether recombinantly-produced or chemically-synthesized, BMP6 or an active portion thereof can be used in a pharmaceutically acceptable composition and administered to a dermal papilla cell or a host, preferably a human, to promote or stimulate hair growth in said host.

For therapeutic use, the BMP6 is generally formulated with a pharmaceutically acceptable vehicle, such as water, buffered saline, polyol (for example, glycerol, propylene glycol, liquid polyethylene glycol and the like) or suitable mixtures thereof. The optimum concentration of BMP6 polypeptide in the chosen vehicle can be determined empirically, according to procedures well-known to medicinal chemists. As used herein, pharmaceutically acceptable vehicle includes any solvent, dispersion medium, and the like which may be appropriate for the desired route of administration of the pharmaceutical preparation. The use of such vehicle for pharmaceutically active substances is known in the art. Suitable vehicles and their formulation are described, for example, in Remington: The Science and Practice of Pharmacy, Alfonso R. Gennaro, editor, 20th ed. Lippingcott Williams & Wilkins: Philadelphia, Pa., 2000.

Pharmaceutical compositions containing BMP6 can be administered by any suitable means, including parenteral injection (such as intraperitoneal, subcutaneous, or intramuscular injection), orally, or by topical application (e.g., transdermal). Desirably, a pharmaceutical composition of the invention is for topical administration in the form of a cream, lotion, liquid, ointment, gel, or aerosol.

Those of ordinary skill in the art can readily optimize effective doses as determined by good medical practice and the clinical condition of the individual patient. Regardless of the manner of administration, it can be appreciated that the actual preferred amounts of BMP6 in a specific case will vary according to the particular formulation and the route of administration. The specific dose for a particular patient depends on age, body weight, general state of health, on diet, on the timing and route of administration, on the rate of excretion, and on medicaments used in combination and the severity of the particular disorder. Dosages for a given subject can be determined using conventional considerations, e.g., by customary comparison of the differential activities of the selected agent and of a known agent, such as by means of an appropriate conventional pharmacological protocol.

The invention is described in greater detail by the following non-limiting examples.

EXAMPLE 1

FACS and Engraftments

Five backskins from P4 K14-H2BGFP/Lef1-RFP double transgenic mice were treated with dispase at 4° C. for 8 hours to separate epidermis/upper follicles from dermis. Dermis was digested with 0.2% collagenase at 37° C. for 40 minutes. Intact follicles and dermal cells were sedimented at 300×g and follicles were obtained at 20×g. Following trypsinization at 37° C. for 5 minutes, cell suspensions were strained. Outer root sheath and matrix cells were selected by FACS as $GFP^{high}RFP^-$ or $GFP^{low}RFP^-$ cells, respectively. Dermal papilla cells were obtained after first removing melanocytes (CD117+), lymphocytes (CD45+) and endothelial cells (CD34+) by antibody-based FACS and then selecting for $GFP^-RFP^{high}$ cells. The dermal fraction enriched in fibroblasts was the RFP⁻GFP⁻ population. For melanocytes isolation, cells were incubated with CD117 followed by staining with streptavidin directly coupled with the fluorochrome APC (1:200, BD PHARMINGEN™, San Diego, Calif.) for 30 minutes. Melanocyte were purified by selecting RFP$^{high}$ CD117(cKit)$^+$ cells. After a final wash, cells were resuspended in phosphate buffered saline (PBS)/fetal calf serum (FCS) and 300 ng/mL propidium iodide for dead cell exclusion.

Cell isolations were performed on a BD FACSVANTAGE SE™ system equipped with BD FACSDIVA™ software (BD Biosciences, San Diego, Calif.). Gates for fluorescence fractionation were set to match those approximated by semi-quantitative immunofluorescence analyses of the cell compartments. Cells were gated for single events and viability and subsequently sorted. Typically >95% cell purity was obtained as determined by post-sort FACS analysis.

Engraftments were performed according to standard methods (Lichti, et al. (1993) supra; Kishimoto, et al. (2000) supra). Experiments included a positive control of cell suspensions from freshly isolated wild-type dermis plus K14-GFPactin keratinocytes and a negative control of keratinocytes alone. 5-10×10$^6$ keratinocytes and 2-4×10$^6$ dermal papilla cells in second to fourth passage were used for grafts. Hair typically appeared after 17 to 24 days.

EXAMPLE 2

RNA Isolation and Microarray Analyses

Total RNA from FACS-sorted cells were purified using the ABSOLUTELY RNA™ Microprep kit (STRATAGENE®, La Jolla, Calif.), and fluorometrically quantified. Quality was assessed by RNA 6000 Pico Assay (Agilent Technologies, Palo Alto, Calif.), and 800 ng were primed with oligo(dT)-T7 primer and reverse transcribed. One round of amplification/labeling was performed to obtain biotinylated CRNA, and 10 μg labeled CRNA was hybridized at 45° C. for 16 hours to mouse genome array MOE430a (AFFYMETRIX®, Inc., Santa Clara, Calif.). Processed chips were read by an argon-ion laser confocal scanner. Two entirely independent datasets were obtained for the five cell populations.

Scanned microarray images were imported into GENE-CHIP® Operating Software (GCOS; AFFYMETRIX®, Inc., Santa Clara, Calif.) to generate signal values and absent/present calls for each probeset using the MAS 5.0 statistical expression algorithm (chp files). Each array was scaled to a target signal of 500 using all probesets and default analysis parameters. For comparisons, raw data and chp files were imported into GENETRAFFIC® 3.8 (Iobion Informatics, La Jolla, Calif.) and replicate microarrays were grouped and compared (Robust Multi-Chip Analysis algorithm). Gene lists were compiled containing probesets >2 fold increased for one over the four other populations. Probesets scoring as increased, but called absent were eliminated. Genes were grouped functionally by uploading probeset lists to the "Database for Annotation, Visualization and Integrated Discovery" (DAVID 1.0) webtool (Dennis, et al. (2003) Genome Biol. 4:P3).

EXAMPLE 3

PCR

All >50 primer pairs were designed to amplify DNA under the same conditions: 3 minutes at 94° C. for initial denaturing; 26-35 cycles of 15 seconds at 94° C. for denaturing, 30 seconds at 60° C. for annealing and 25 seconds at 72° C. for extension. Amplifications with minus reverse transcriptase control cDNAs yielded no products for any of the primer pairs at the cycles tested. For real-time PCR, the same primers were employed using the LIGHTCYCLER™ System (Roche Diagnostics, Indianapolis, Ind.), LIGHTCYCLER™ 3.5 software and the LIGHTCYCLER™ DNA Master SYBR Green I reagents. Differences between samples and controls were calculated based on the $2^{-\Delta\Delta CP}$ method.

EXAMPLE 4

Immunofluorescence and in situ Hybridizations

Tissues were processed according to standard methods (Vaezi, et al. (2002) Dev. Cell 3:367-381; DasGupta and Fuchs (1999) Development 126:4557-4568). Antibodies used were: Alx4 (Mouse, 1:100; Exalpha Biologicals, Inc., Maynard, Mass.), BrdU (Rat, 1:200; ABCAM®, Cambridge, Mass.), CD104 (Rat, 1:100; BD PHARMINGEN™, San Diego, Calif.), Hhip (Goat, 1:200; R&D Systems, Minneapolis, Minn.), Ki67 (Rabbit, 1:500; NOVOCASTRA™, Newcastle upon Tyne, UK), K5 (Rabbit, 1:5000), p75 (rabbit, 1:100; Oncogene Research Products, Boston, Mass.), pSmad1,5,8 (Rabbit, 1:50; Cell Signaling Technologies, Beverly, Mass.), Tyrosinase (Rabbit, 1:500), Vimentin (Rabbit, 1:500, Biomeda, Foster City, Calif.), Wif1 (Goat, 1:200; R&D Systems, Minneapolis, Minn.), HoxA9 (Rabbit, 1:200; R&D Systems, Minneapolis, Minn.). FITC or TEXASRED® conjugated anti-mouse, -rat, -rabbit or anti-goat secondary antibodies (1:200; Jackson Laboratories, Bar Harbor, Me.). Probes for in situ hybridizations were generated from IMAGE cDNA clones (IMAGE consortium, ATCC®, Manassas, Va.) using the DIG RNA labeling kit (SP6/T7; Roche Diagnostics, Indianapolis, Ind.): BMP6 (Image: 2779955), Gfra1 (Image:6390018), Hhip (Image:6402422), Mdk (Image:4167496), Prss12 (Image:3665834). Imaging was performed using Axioskop and Axiophot microscopes (Zeiss).

EXAMPLE 5

Cell Culture

Viability of FACS-isolated dermal papilla cells was assessed by Trypan Blue staining and equal numbers of live cells (5000/cm$^2$) were plated in Amniomax™ C-100 medium (INVITROGEN™, Carlsbad, Calif.), a medium established for use with dog whisker dermal papilla cells (Bratka-Robia, et al. (2002) Vet. Dermatol. 13:1-6) and found to be the best of five media tested. At approximately 30% confluence (2-4 days) cells were fed with medium±growth factors (R&D Systems). Experiments were performed in triplicate and ≧3x.

What is claimed is:

1. A method for isolating dermal papilla cells comprising
    (a) obtaining a population of cells comprising dermal papilla cells;
    (b) sorting the population of cells by
        (i) removing cells that express CD34,
        (ii) removing cells that express CD45, and
        (iii) removing cells that express CD117 to obtain a population of cells that are CD34⁻, CD45⁻ and CD117⁻; and
    (c) isolating from the population of CD34⁻, CD45⁻ and CD117⁻cells, a population of cells that express Hhip, Frzb, Pdgfra, Tgfbr1, Vcam1, Itga9, Epha7, and Efnb3, thereby isolating dermal papilla cells.

* * * * *